(12) United States Patent
Ra

(10) Patent No.: US 11,141,351 B2
(45) Date of Patent: Oct. 12, 2021

(54) SYRINGE

(71) Applicant: Yong-Kuk Ra, Gumi-si (KR)

(72) Inventor: Yong-Kuk Ra, Gumi-si (KR)

(*) Notice: Subject to any disclaimer, the term of this patent is extended or adjusted under 35 U.S.C. 154(b) by 697 days.

(21) Appl. No.: 15/768,600

(22) PCT Filed: Oct. 27, 2016

(86) PCT No.: PCT/KR2016/012127
§ 371 (c)(1),
(2) Date: Apr. 16, 2018

(87) PCT Pub. No.: WO2017/078322
PCT Pub. Date: May 11, 2017

(65) Prior Publication Data
US 2018/0303714 A1    Oct. 25, 2018

(30) Foreign Application Priority Data
Nov. 4, 2015 (KR) .................. 10-2015-0154818

(51) Int. Cl.
*A61J 1/20* (2006.01)
*A61M 5/32* (2006.01)
(Continued)

(52) U.S. Cl.
CPC .......... *A61J 1/2096* (2013.01); *A61J 1/2037* (2015.05); *A61M 5/1782* (2013.01);
(Continued)

(58) Field of Classification Search
CPC ...... A61M 5/3291; A61M 5/32; A61M 39/22; A61M 5/3297; A61M 2005/3201;
(Continued)

(56) References Cited

U.S. PATENT DOCUMENTS

2012/0179096 A1* 7/2012 Aeschlimann .......... A61M 5/32
604/87

FOREIGN PATENT DOCUMENTS

KR    10-1171150      8/2012
KR    101335979 B1 * 12/2013 .......... A61M 5/3293
(Continued)

OTHER PUBLICATIONS

International Search Report for International Application No. PCT/KR2016/012127, dated Feb. 3, 2017.
(Continued)

*Primary Examiner* — Lauren P Farrar
(74) *Attorney, Agent, or Firm* — LRK Patent Law Firm

(57) ABSTRACT

The present invention relates to a syringe, and more particularly, to an apparatus obtained by improving an conventional syringe formed with an injection flow passage including an injection needle, so as to share a portion of the injection flow passage except the injection needle or to form a suction flow passage completely independent of the injection flow passage, thereby further smoothing suction of a liquid medicine. The syringe is configured such that the separate suction flow passage bypassing the injection needle is formed in an conventional syringe to more smoothly perform the suction of the liquid medicine, thereby maximizing user's convenience and marketability of the product.

8 Claims, 13 Drawing Sheets

(51) Int. Cl.
 *A61M 39/22* (2006.01)
 *A61M 5/178* (2006.01)
 *A61M 5/31* (2006.01)
 *A61M 5/28* (2006.01)
 *A61M 5/34* (2006.01)

(52) U.S. Cl.
 CPC .............. *A61M 5/286* (2013.01); *A61M 5/31* (2013.01); *A61M 5/32* (2013.01); *A61M 5/3202* (2013.01); *A61M 5/3291* (2013.01); *A61M 5/3297* (2013.01); *A61M 5/349* (2013.01); *A61M 39/22* (2013.01); *A61M 2005/3128* (2013.01); *A61M 2005/3201* (2013.01); *A61M 2205/0216* (2013.01)

(58) Field of Classification Search
 CPC ........ A61M 2005/3128; A61M 5/1782; A61M 5/286; A61M 5/31; A61M 5/3202; A61M 5/349; A61M 2205/0216; A61J 1/2096; A61J 1/2037
 See application file for complete search history.

(56) References Cited

FOREIGN PATENT DOCUMENTS

| | | |
|---|---|---|
| KR | 10-2015-0018336 | 2/2015 |
| KR | 10-1560149 | 10/2015 |
| KR | 10-1560150 | 10/2015 |
| KR | 10-1563723 | 10/2015 |

OTHER PUBLICATIONS

English translation of the Written Opinion of International Application No. PCT/KR2016/012127, dated May 8, 2018.

* cited by examiner

FIG. 7
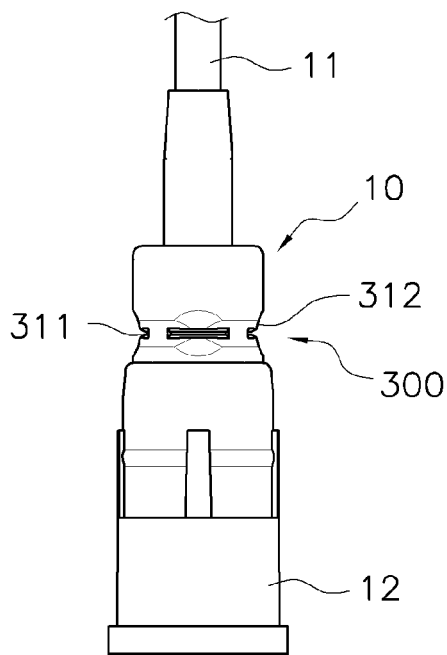
(a)
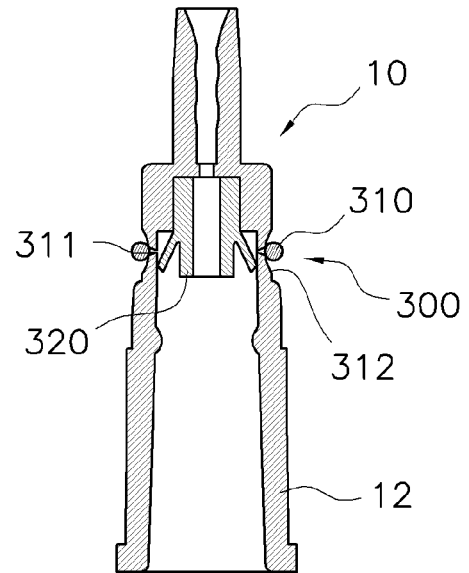
(b)

SYRINGE

TECHNICAL FIELD

The present invention relates to a syringe, and more particularly, to an apparatus obtained by improving an conventional syringe formed with an injection flow passage including an injection needle, so as to share a portion of the injection flow passage except the injection needle or to form a suction flow passage completely independent of the injection flow passage, thereby further smoothing suction of a liquid medicine, wherein the apparatus is configured such that a separate suction flow passage bypassing the injection needle is formed in the conventional syringe to more smoothly perform the suction of the liquid medicine, thereby maximizing user's convenience and marketability of the product.

BACKGROUND ART

In general, a syringe is an instrument for injecting a liquid medicine into a body of an animal/plant and is configured to pierce a skin with a sharp tip thereof to allow the liquid medicine to be injected into any tissue of the body.

FIG. 1 is an exploded perspective view illustrating a conventional syringe. As shown in FIG. 1, the syringe generally includes a cylinder 20 to which an injection needle 10 is coupled and in which an injection liquid is contained, and a plunger 30 provided in the cylinder 20 so as to be movable forward and backward.

In this conventional syringe, as the plunger 30 is retreated, a negative pressure is generated in the cylinder 20 and the cylinder is then filled with the injection liquid. As the plunger is moved forward, the injection liquid in the cylinder 20 is discharged through the injection needle by a positive pressure and then injected into a patient's body.

In use of this conventional syringe, however, if a diameter of the injection needle 10 is very small, the inside of the cylinder 20 is in a vacuum state due to the negative pressure but the suction of the liquid medicine is not performed smoothly even though a user retreats the plunger 30 in order to suck the liquid medicine.

Accordingly, there are problems in that it takes a long time to suck the liquid medicine, which is inconvenient to the user, and furthermore when the user releases the plunger 30 before the suction of the liquid medicine is completed, the plunger 30 is advanced by itself in a state where the liquid medicine is not sucked into the cylinder 20.

In addition, Korean Patent Publication No. 10-1563723 issued to the present applicant has solved these problems, but it has been pointed out that a filtering injection needle assembly is configured to cause a liquid medicine to pass through a filter mean upon suction of the liquid medicine, resulting in unsmooth suction of the liquid medicine due to the filter means.

PRIOR ART DOCUMENT

Korean Patent Publication No. 10-1563723.

DISCLOSURE

Technical Problem

The present invention is conceived to solve these problems, and an object of the present invention is to provide a syringe configured such that a separate suction flow passage bypassing an injection needle is formed in an conventional syringe to more smoothly perform suction of a liquid medicine, thereby maximizing user's convenience and marketability of the product.

Technical Solution

According to the present invention, there is provided a syringe including an injection needle and a cylinder and formed with an injection flow passage extending from the cylinder to the injection needle, wherein the syringe further includes an opening/closing means for selectively opening or closing the injection flow passage; and a suction flow passage formed from a pointed hollow cap to the cylinder and provided with a through-hole formed in any one of the injection needle, a connector for connecting the injection needle to the cylinder, and the cylinder to establish communication between an inside and an outside thereof and a one-way valve means for intermittently controlling opening or closing of the through-hole.

The one-way valve means is preferably opened in response to coupling of the cap and is closed in response to separation of the cap. More specifically, it is preferred that the one-way valve means includes an elastic band having a circular cross-section and configured to surround and elastically seal the through-hole, an engagement ledge formed on an inner peripheral surface of the cap so as to be brought into contact with and move the elastic band in response to an axial movement of the cap, and a groove configured to elastically return the elastic band to a position at which the elastic band hermetically seals the through-hole.

Similarly, the one-way valve means may be opened by a negative pressure applied in the cylinder of the syringe and may be closed by a positive pressure applied in the cylinder of the syringe. More specifically, the one-way valve means may be a known check valve including an elastic flap for selectively opening or closing the through-hole, or the one-way valve means may be a known check valve comprising a sphere for selectively opening or closing the through-hole.

Otherwise, the one-way valve means may be opened or closed depending on a change in alignment of the flow passages in response to a rotation manipulation.

Alternatively, the one-way valve means may include an elastic sealing member fixed to maintain airtightness of the through-hole and a penetration needle configured to penetrate the elastic sealing member, whereby the one-way valve means may be opened in response to insertion of the penetration needle into the elastic sealing member and may be closed in response to separation of the penetration needle from the elastic sealing member.

In addition, it is most preferable that the cap accommodates the opening/closing means to form a portion of the suction flow passage in a space between an outer perimeter of the opening/closing means and an inner perimeter of the cap; and an adhesive material for fixing an needle body and a hub of the injection needle to each other is accommodated in the opening/closing means to be isolated from a liquid medicine.

Advantageous Effects

The syringe of the present invention configured such that a separate suction flow passage bypassing an injection needle is formed in an conventional syringe performs more smooth suction of a liquid medicine, thereby maximizing user's convenience and marketability of the product.

DESCRIPTION OF DRAWINGS

FIGS. 7 (a) and (b) are views illustrating an example in which two one-way valve means are employed in the first embodiment of the syringe according to the present invention.

BEST MODE

Figure 1:
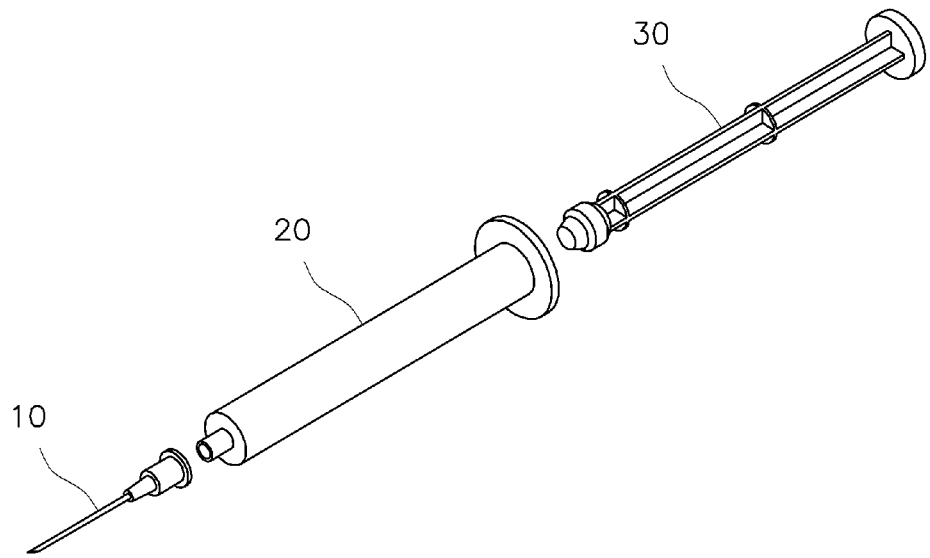
FIG. 1 is an exploded perspective view illustrating a conventional syringe.
Figure 2:
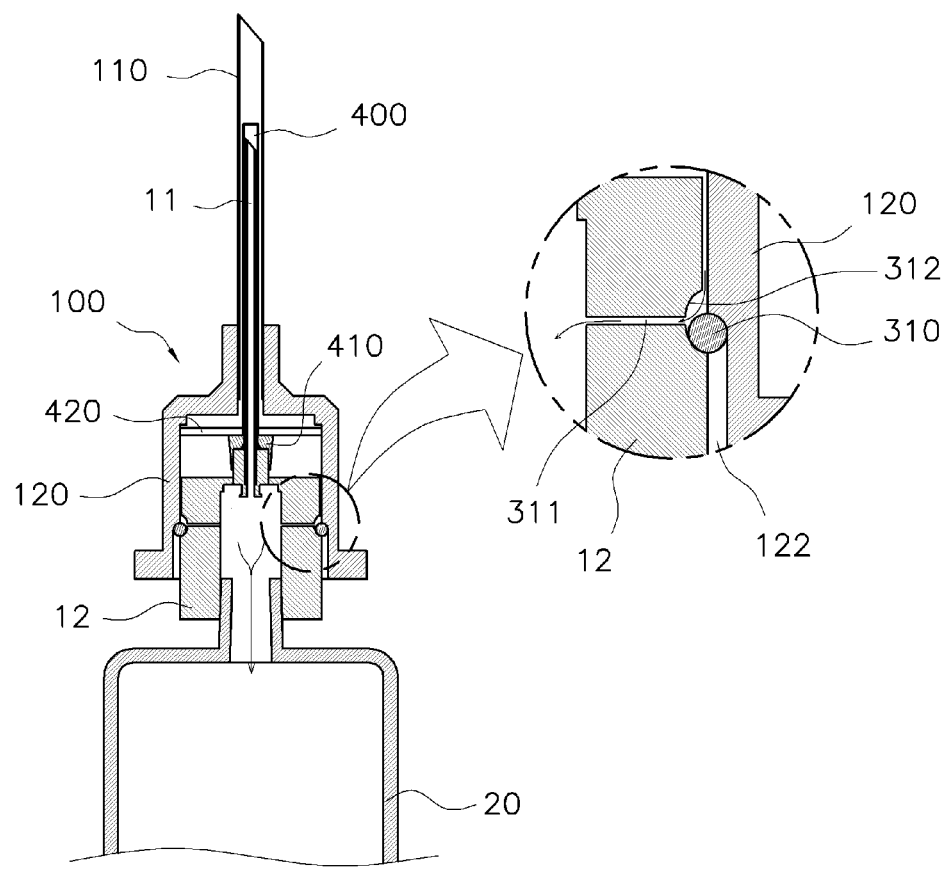
FIG. 2 is a sectional view illustrating a state where a one-way valve means is opened in a first embodiment of a syringe according to the present invention.
Figure 3:
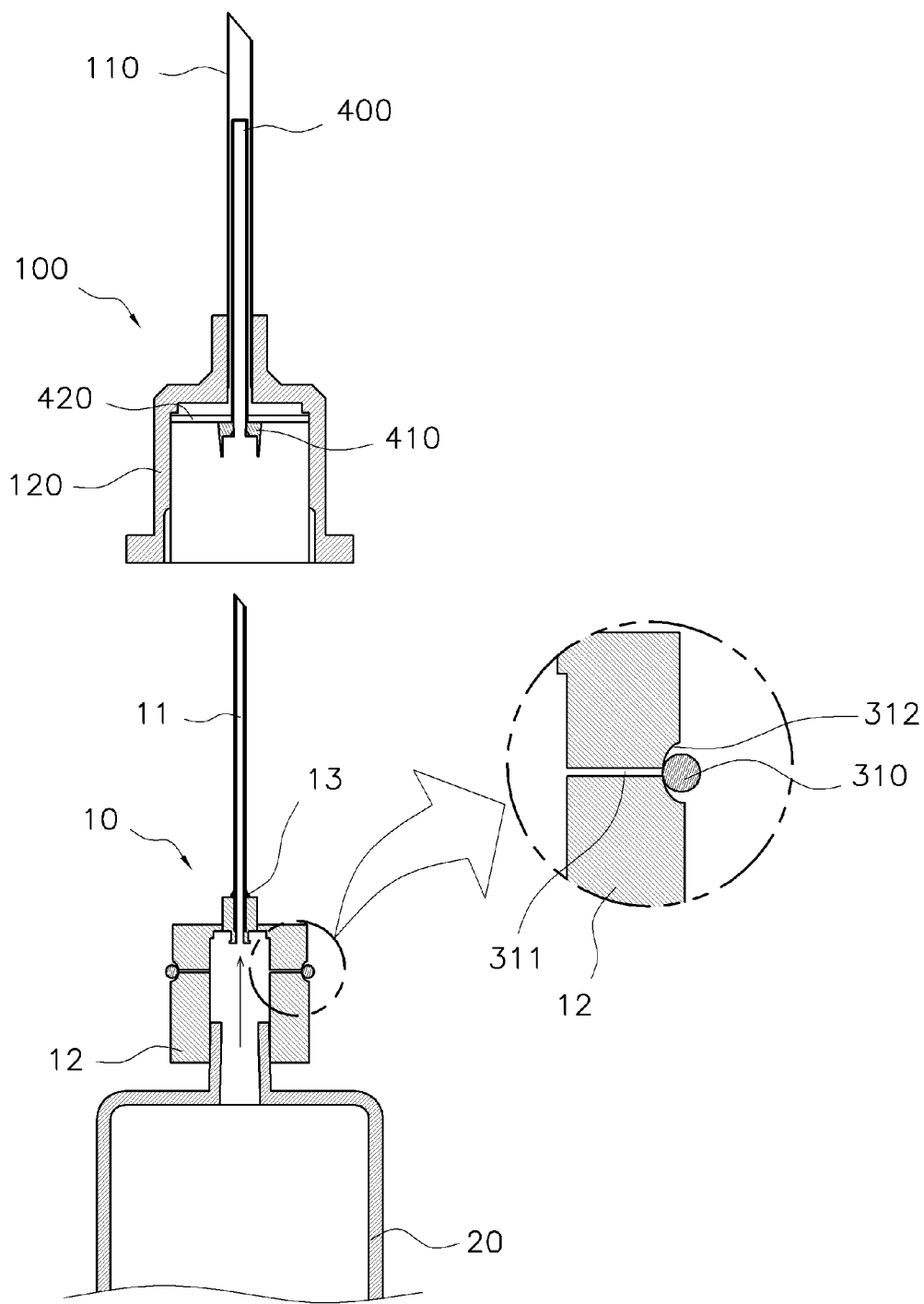
FIG. 3 is a sectional view illustrating a state where the one-way valve means is closed in the first embodiment of the syringe according to the present invention.
Figure 4:
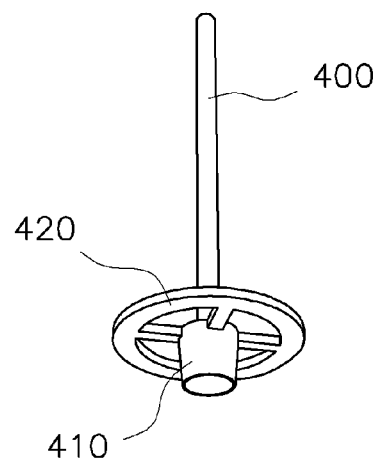
FIG. 4 is a perspective view exemplarily illustrating an opening/closing means in the first embodiment of the syringe according to the present invention.

FIG. 2 is a sectional view illustrating a state where a one-way valve means is opened in a first embodiment of a syringe according to the present invention, FIG. 3 is a sectional view illustrating a state where the one-way valve means is closed in the first embodiment of the syringe according to the present invention, and FIG. 4 is a perspective view exemplarily illustrating an opening/closing means in the first embodiment of the syringe according to the present invention.

Figure 5:
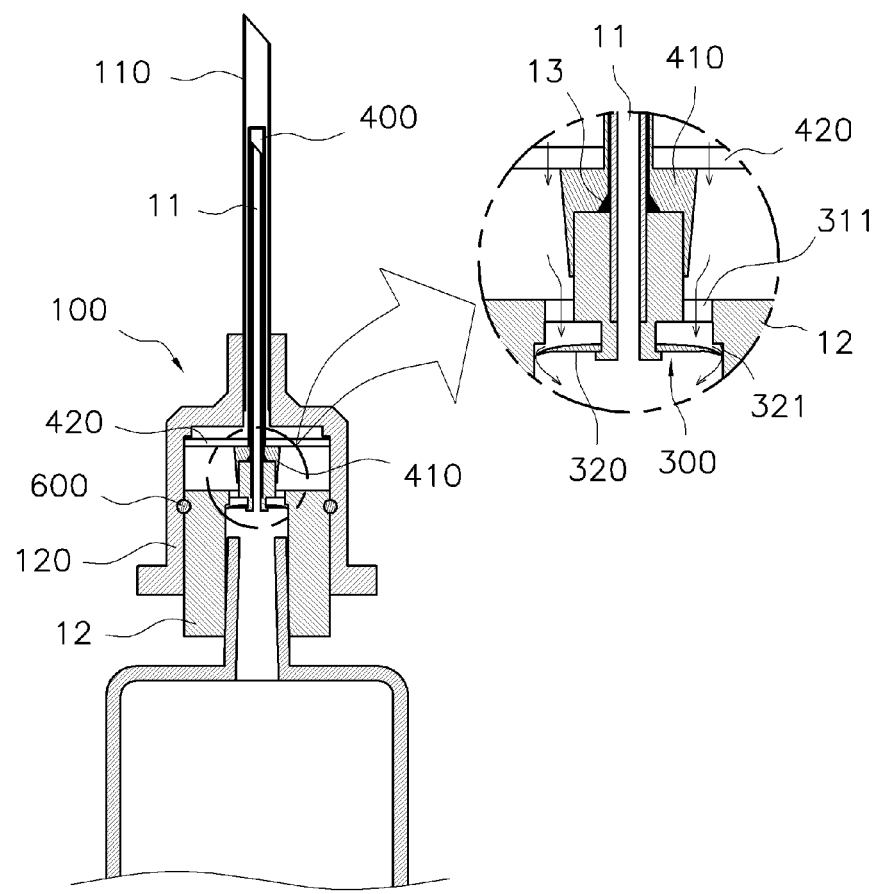
FIG. 5 is a sectional view illustrating a state where another example of the one-way valve means is opened in the first embodiment of the syringe according to the present invention.
Figure 6:
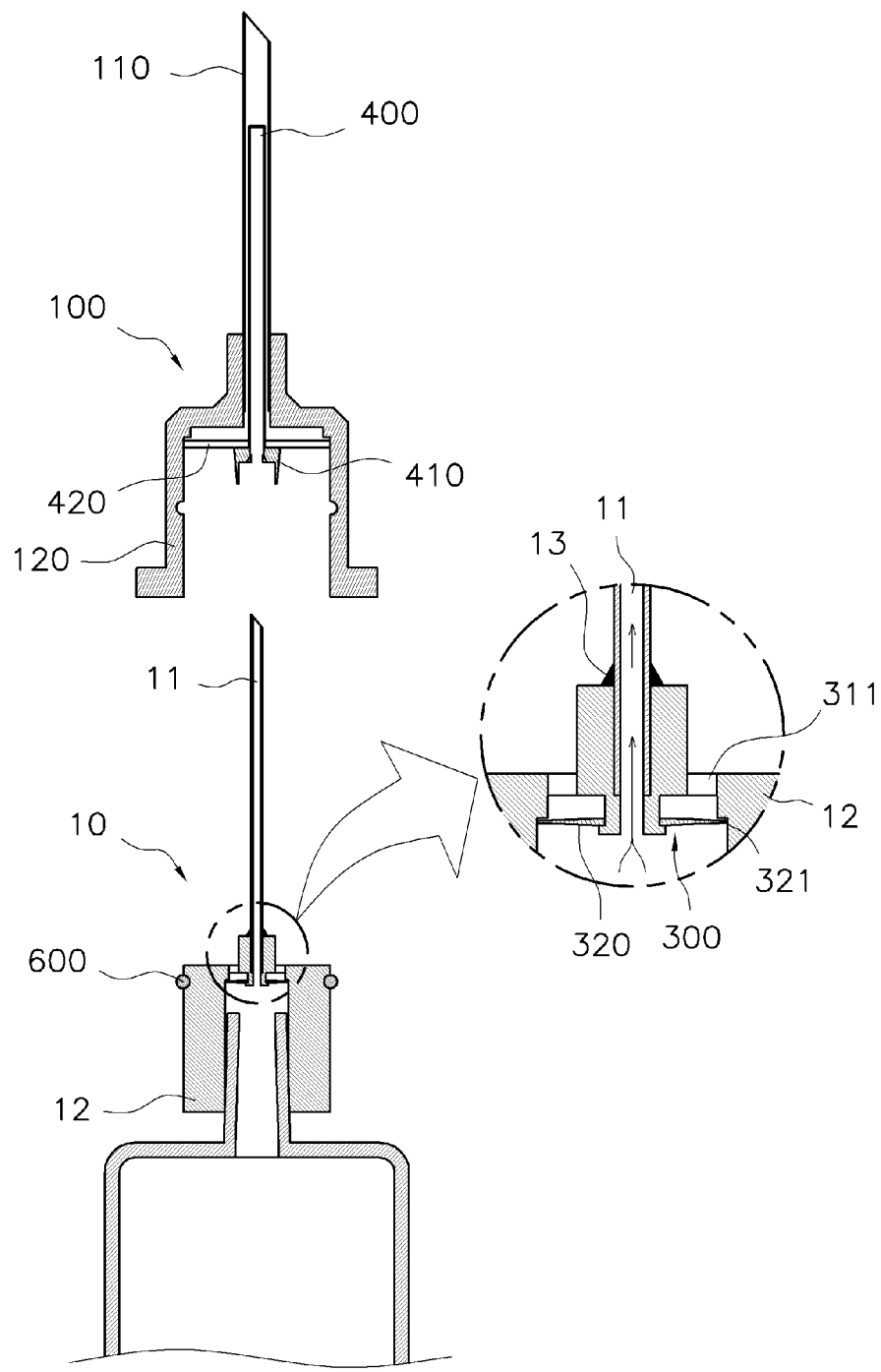
FIG. 6 is a sectional view illustrating a state where the other example of the one-way valve means is closed in the first embodiment of the syringe according to the present invention.

Moreover, FIG. 5 is a sectional view illustrating a state where another example of the one-way valve means is opened in the first embodiment of the syringe according to the present invention, FIG. 6 is a sectional view illustrating a state where the other example of the one-way valve means is closed in the first embodiment of the syringe according to the present invention, and FIG. 7 is views illustrating an example in which two one-way valve means are employed in the first embodiment of the syringe according to the present invention, wherein FIG. 7 (a) is a front view and FIG. 7 (b) is a sectional view.

Figure 8:
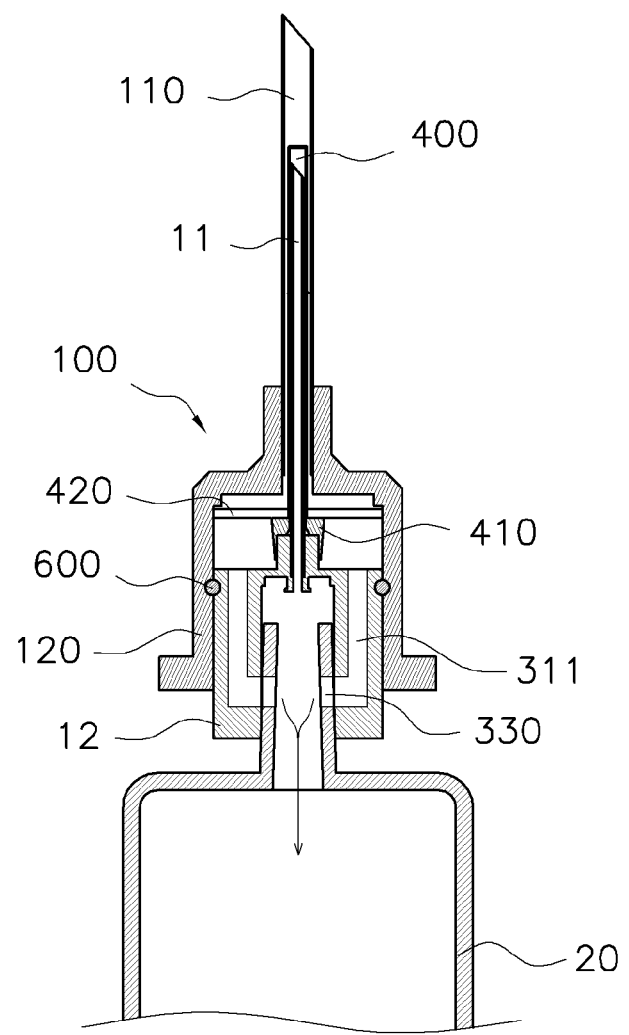
FIG. 8 is a sectional view illustrating a state where a further example of the one-way valve means is opened in the first embodiment of the syringe according to the present invention.
Figure 9:
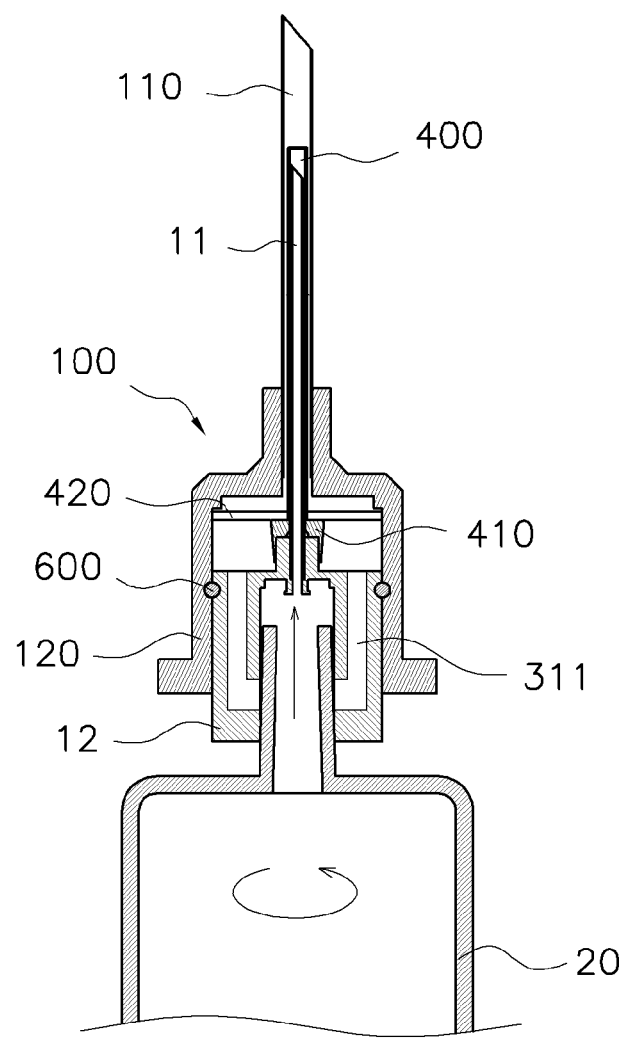
FIG. 9 is a sectional view illustrating a state where the further example of the one-way valve means is closed in the first embodiment of the syringe according to the present invention.

Furthermore, FIG. 8 is a sectional view illustrating a state where a further example of the one-way valve means is opened in the first embodiment of the syringe according to the present invention, and FIG. 9 is a sectional view illustrating a state where the further example of the one-way valve means is closed in the first embodiment of the syringe according to the present invention.

Figure 10:
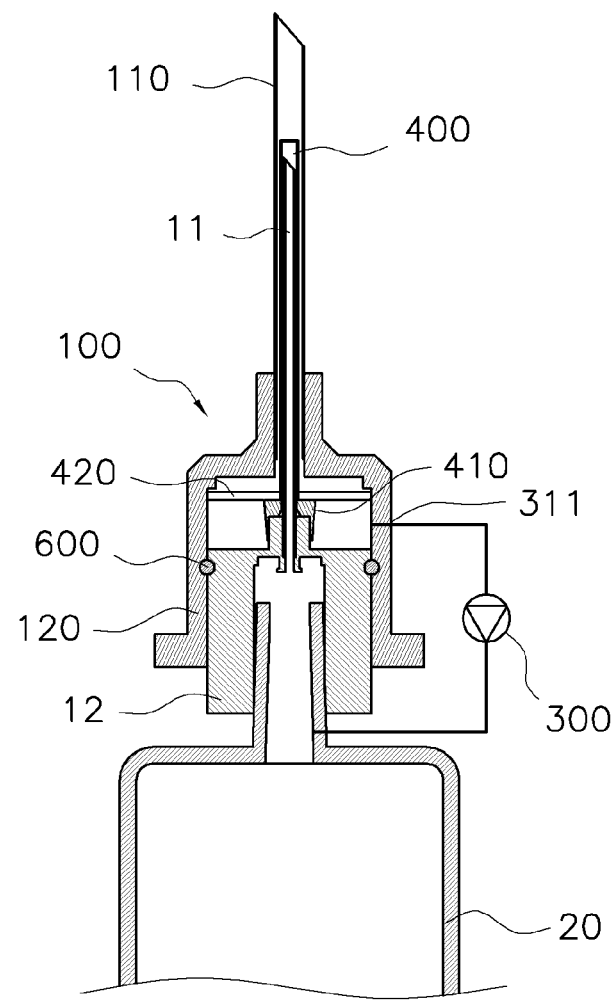
FIG. 10 is a sectional view illustrating a state where the one-way valve means is externally provided in the first embodiment of the syringe according to the present invention.
Figure 11:
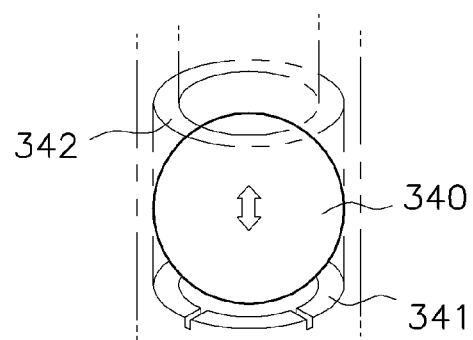
FIG. 11 is a view illustrating a still further example of the one-way valve means in the first embodiment of the syringe according to the present invention.
Figure 12:
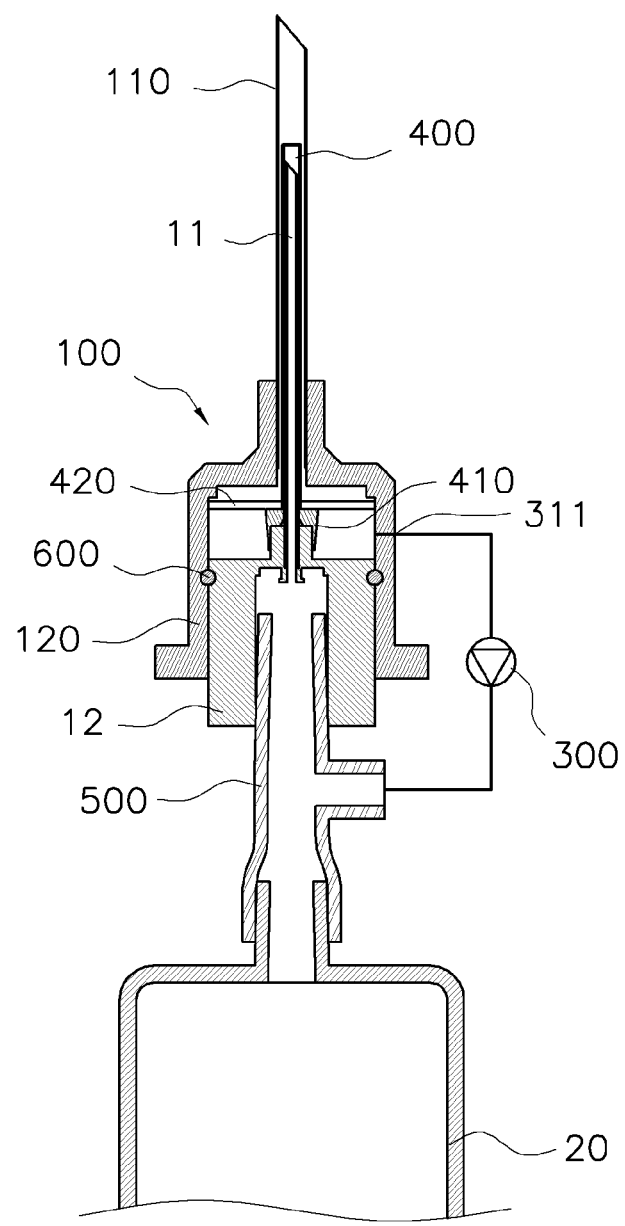
FIG. 12 is a sectional view illustrating a state where the one-way valve means is externally provided and a connector is employed in the first embodiment of the syringe according to the present invention.

In addition, FIG. 10 is a sectional view illustrating a state where the one-way valve means is externally provided in the first embodiment of the syringe according to the present invention, FIG. 11 is a view illustrating a still further example of the one-way valve means in the first embodiment of the syringe according to the present invention, and FIG. 12 is a sectional view illustrating a state where the one-way valve means is externally provided and a connector is employed in the first embodiment of the syringe according to the present invention.

Figure 13:
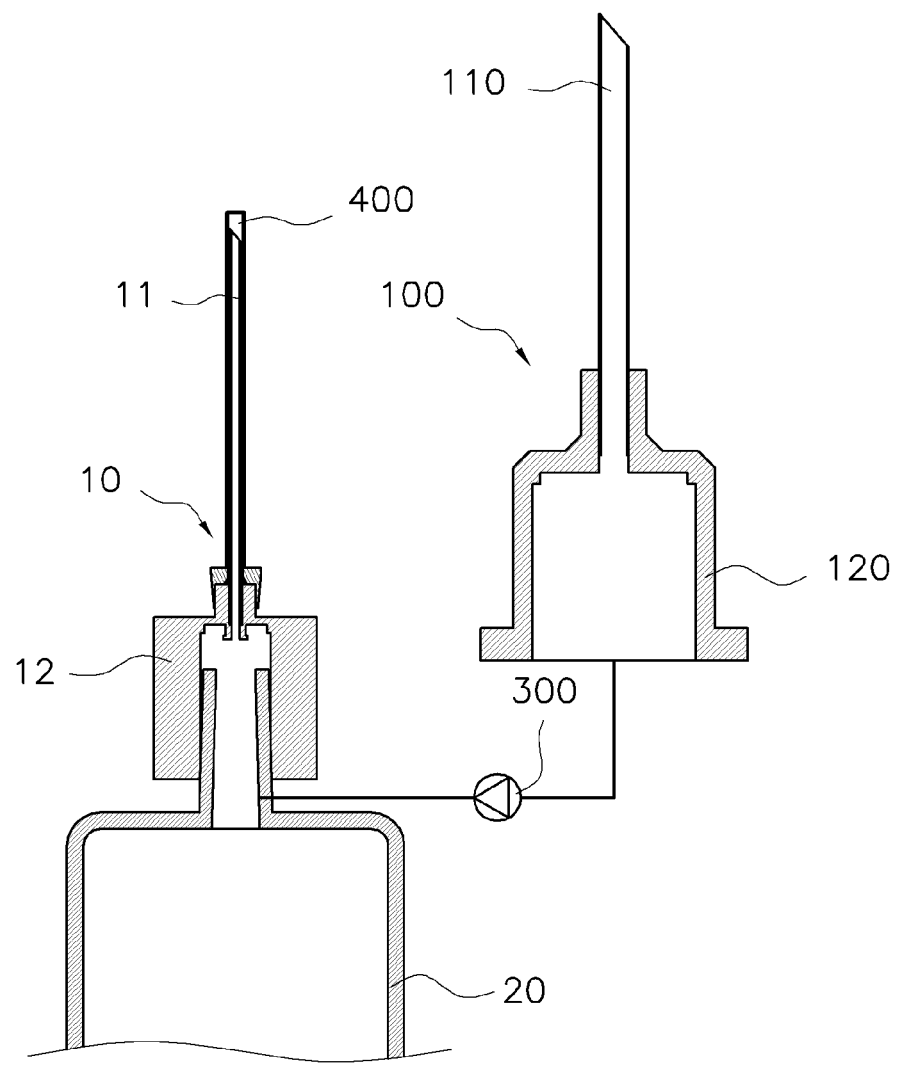
FIG. 13 is a sectional view illustrating a state where a one-way valve means is externally provided in a second embodiment of the syringe according to the present invention.
Figure 14:
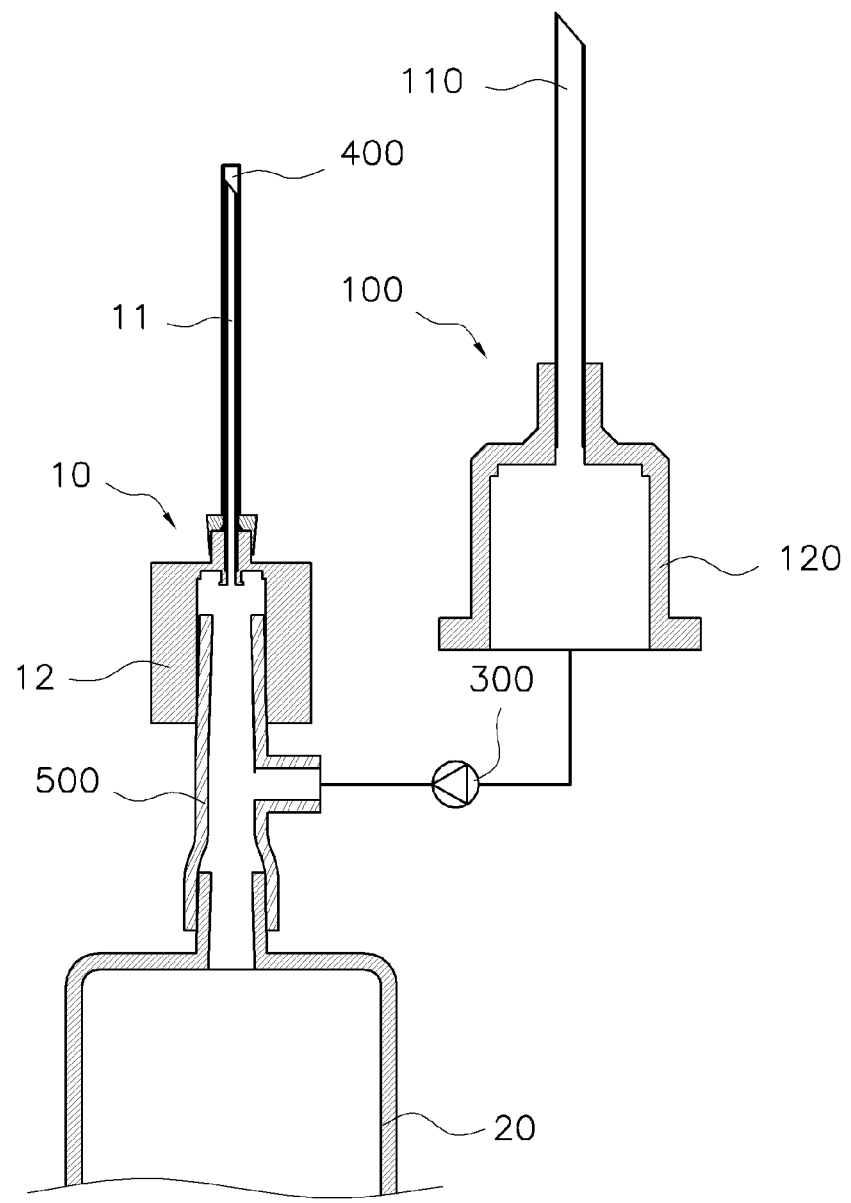
FIG. 14 is a sectional view illustrating a state where the one-way valve means is externally provided and a connector is employed in the second embodiment of the syringe according to the present invention.

FIG. 13 is a sectional view illustrating a state where a one-way valve means is externally provided in a second embodiment of the syringe according to the present invention, and FIG. 14 is a sectional view illustrating a state where the one-way valve means is externally provided and a connector is employed in the second embodiment of the syringe according to the present invention.

Figure 15:
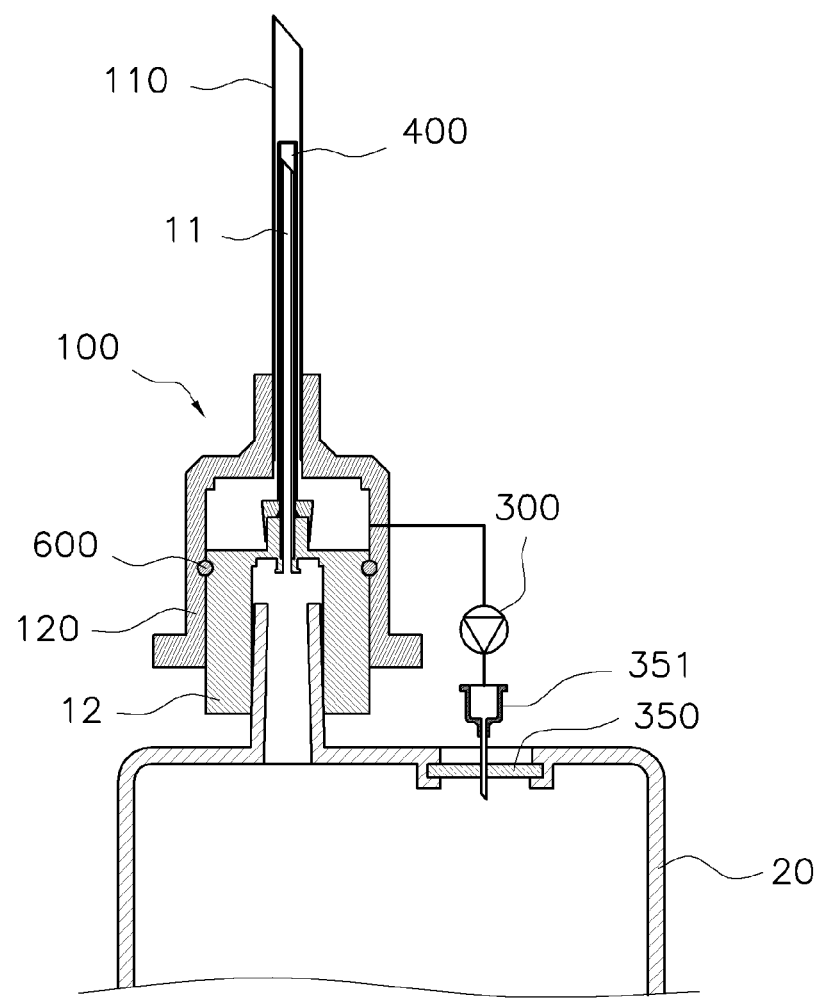
FIG. 15 is a sectional view illustrating an example of a one-way valve means in a third embodiment of the syringe according to the present invention.
Figure 16:
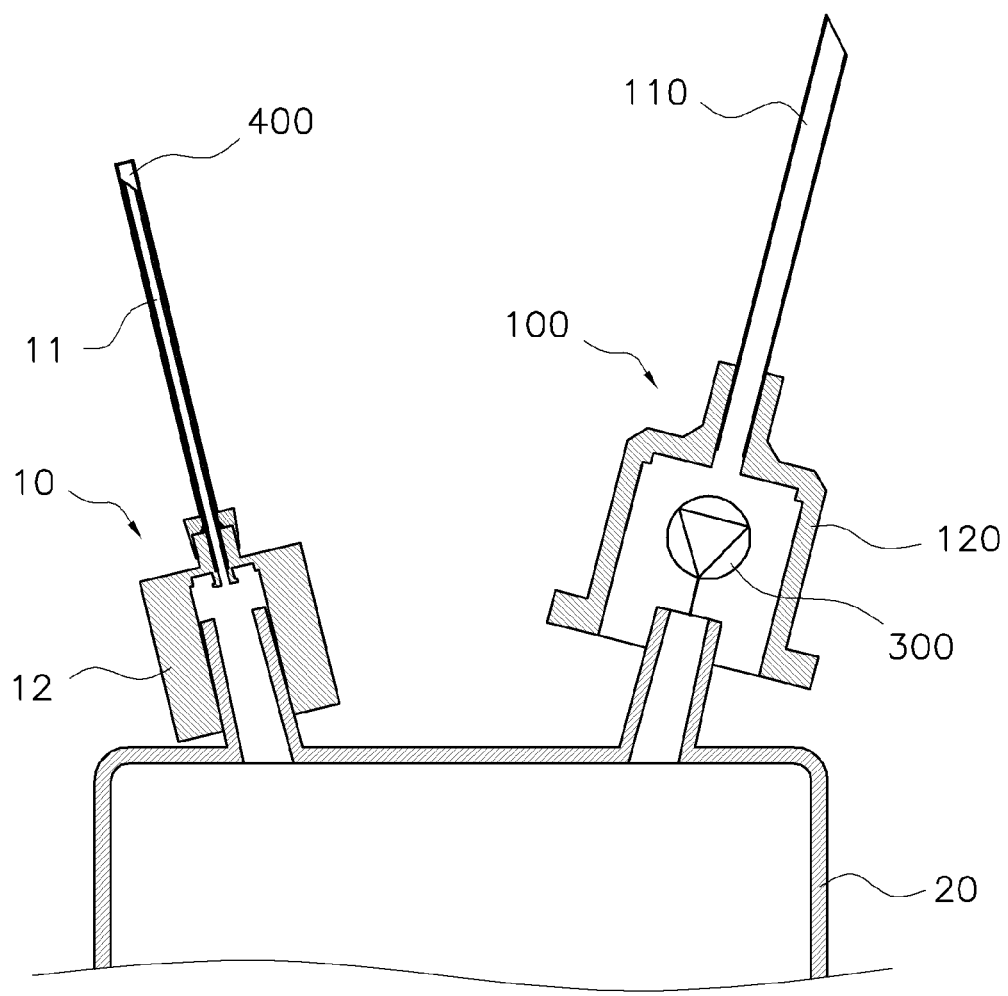
FIG. 16 is a sectional view illustrating a state where a one-way valve means is internally provided in a fourth embodiment of the syringe according to the present invention.

Finally, FIG. 15 is a sectional view illustrating an example of a one-way valve means in a third embodiment of the syringe according to the present invention, and FIG. 16 is a sectional view illustrating a state where a one-way valve means is internally provided in a fourth embodiment of the syringe according to the present invention.

Embodiments of the present invention will be described below in detail with reference to the accompanying drawings.

As shown in FIGS. 2 to 16, a syringe according to the present invention is technically characterized in that a separate suction flow passage bypassing an injection needle is formed in an conventional syringe so as to perform smooth suction of a liquid medicine with a less force, thereby maximizing user's convenience and marketability of a product.

The syringe of the present invention includes an injection needle 10 and a cylinder 20 and is formed with an injection flow passage extending from the cylinder 20 to the injection needle 10. The syringe further includes an opening/closing means 400 for selectively opening or closing the injection flow passage; and a suction flow passage formed from a pointed hollow cap 100 to the cylinder 20 and provided with a through-hole formed in any one of the injection needle 10, a connector 500 for connecting the injection needle 10 to the cylinder 20, and the cylinder 20 to establish communication between an inside and an outside thereof and a one-way valve means 300 for intermittently controlling opening or closing of the through-hole.

That is, the present invention addresses an issue that a long time or a large force is required to suck the liquid medicine as the liquid medicine is sucked into the cylinder 20 only through the elongated injection needles 10, by additionally providing the opening/closing means 400 configured to temporarily close the injection needle 10 upon suction of the liquid medicine and by forming the suction flow passage capable of sucking the liquid medicine without passing through the injection needle 10, whereby it is possible to easily and quickly perform the suction of the liquid medicine with a less force.

To this end, in the present invention, the through-hole provided on the suction flow passage is opened by the one-way valve means 300 upon suction of the liquid medicine, and thus the liquid medicine is easily sucked into the cylinder 20 of the syringe without passing through the injection needle 10 and the opening/closing means 400 closes the injection needle 10 during this time.

On the contrary, upon injection of the liquid medicine, the through-hole is closed by the one-way valve means 300 to block the suction flow passage, while as the user removes the opening/closing means 400, the injection needle 10 is opened and the liquid medicine is then injected.

According to embodiments, opening or closing of the one-way valve means 300 may be adjusted depending on simply whether the cap 100 is separated, may be automatically adjusted depending on a direction of pressure on the cylinder 20, or may be adjusted in response to a user's rotation manipulation. In addition, the one-way valve means may be a pointed penetration needle 351 for penetrating a soft elastic sealing material 350.

In implementing the syringe of the present invention as described above, there may be the following four examples depending on combinations of whether an inlet of the suction flow passage and an outlet of the injection flow passage are coaxially arranged with each other and whether an outlet of the suction flow passage and an inlet of the injection flow passage are shared on the cylinder 20 of the syringe. These examples will be described below by classifying them into first to fourth embodiments.

First Embodiment

Example in which the inlet of the suction flow passage and the outlet of the injection flow passage are coaxially arranged with each other, and the outlet of the suction flow passage and the inlet of the injection flow passage are shared.

Second Embodiment

Example in which the inlet of the suction flow passage and the outlet of the injection flow passage are not coaxially arranged with each other, and the outlet of the suction flow passage and the inlet of the injection flow passage are shared.

Third Embodiment

Example in which the inlet of the suction flow passage and the outlet of the injection flow passage are coaxially arranged with each other, and the outlet of the suction flow passage and the inlet of the injection flow passage are not shared.

Fourth Embodiment

Example in which the inlet of the suction flow passage and the outlet of the injection flow passage are not coaxially arranged with each other, and the outlet of the suction flow passage and the inlet of the injection flow passage are not shared.

(1) First Embodiment

Example in which the inlet of the suction flow passage and the outlet of the injection flow passage are coaxially arranged with each other, and the outlet of the suction flow passage and the inlet of the injection flow passage are shared.

The first embodiment of the syringe of the present invention may be further classified into an example in which the one-way valve means 300 is embedded in the syringe and an example in which the one-way valve means 300 is externally provided.

First, the example of the first embodiment of the syringe according to the present invention in which the through-hole and the one-way valve means 300 are embedded in the syringe is illustrated in FIGS. 2 to 9.

Particularly, in the first embodiment of the syringe according to the present invention, the example in which the one-way valve means 300 opens the through-hole in response to coupling of the cap 100 and closes the through-hole in response to separation of the cap 100 is shown in FIGS. 2 to 4.

This may be implemented in various ways into the one-way valve being opened or closed by coupling or separating the hollow cap 100 having a diameter larger than that of the injection needle 10 in an axial direction of the injection needle 10.

In particular, as illustrated in FIG. 2, it is preferable that the one-way valve means 300 includes an elastic band 310 having a circular cross-section and configured to surround and elastically seal the through-hole 311, an engagement ledge 122 formed on an inner peripheral surface of the cap 100 such that the engagement ledge comes into contact with the elastic band 310 in response to an axial movement of the cap 100 and moves the elastic band 310, and a groove 312 configured to elastically return the elastic band 310 to a position at which the elastic band hermetically seals the through-hole.

The suction flow passage consists of a suction needle 110 of the cap 100→a cap hub 120 of the cap 100→the one-way valve means 300→a hub 12 of the injection needle 10→the cylinder 20.

The cap 100 is to suck the liquid medicine from a liquid medicine-container, and includes the suction needle 110 and the cap hub 120. A tip of the suction needle 110 is inclined and pointed to penetrate a vial or the like, and is made of a metal material or a synthetic resin material so that it has a high strength.

In addition, the cap hub 120 is integrally coupled to and supports the suction needle 110, wherein an inner peripheral surface of the cap hub 120 is coupled to an outer peripheral surface of the hub 12 that supports a needle body 11 of the injection needle 10.

Here, the needle body 11 and the hub 12 of the injection needle 10 are fixed to each other by an adhesive material 13 such as epoxy, wherein the hub 12 is hermetically assembled to the cylinder 20 of the syringe.

In addition thereto, although the needle body 11 of the injection needle 10 is closed by the opening/closing means 400 upon suction of the liquid medicine, the opening/closing means 400 is separated to open the needle body 11 upon injection of the liquid medicine.

In particular, in the present invention, the opening/closing means 400 may be configured to include a hermetic space 410 and a flange 420 as illustrated in FIG. 4.

In other words, the opening/closing means 400 has functions of closing the needle body 11 of the injection needle 10 upon suction of the liquid medicine and of opening the needle body 11 of the injection needle 10 upon injection of the liquid medicine. In the present invention, it is preferable that the opening/closing means 400 can be coupled to the hub 12 of the injection needle 10.

To this end, the hermetic space 410 is formed at a lower portion of the opening/closing means 400 so that the hermetic space 410 may surround and be coupled to the hub 12 of the injection needle 10.

In particular, in the present invention, it is preferable that the adhesive material 13 for securing the needle body 11 and the hub 12 of the injection needle 10 to each other is accommodated in the hermetic space 410 of the opening/closing means 400, which surrounds the injection needle 10 to maintain airtightness, so that the adhesive material is isolated from the liquid medicine.

With this configuration, it is possible to prevent degradation of an adhesive force of the adhesive material 13 due to contact of the adhesive material 13 with the liquid medicine, or alteration of components of the liquid medicine caused by the adhesive material 13.

In addition thereto, the flange 420 provided in the opening/closing means 400 enables the opening/closing means 400 to be secured to the inner peripheral surface of the cap hub 120, if necessary.

FIG. 3 illustrates that the opening/closing means 400 is fixedly installed within the cap 100 so that the opening/closing means 400 is separated together with the cap 100 in response to separation of the cap 100, thereby opening the injection needle 10.

As illustrated in FIGS. 2 and 3, the hub 12 of the injection needle 10 is provided with the through-hole 311 formed to extend from the inner peripheral surface to the outer peripheral surface of the hub, and the groove 312 is formed on the outer peripheral surface of the hub 12 along an entire perimeter of the hub around the through-hole 311.

The through-hole 311 may be appropriately changed in number and size such that the liquid medicine may flow smoothly and airtightness may be achieved, and the groove 352 is formed to have a gently curved surface. The elastic band 310 made of an elastic material such as rubber having a generally circular cross-section is placed in the groove 312.

This elastic band 310 is elastically disposed in the groove 312 so that the position of the elastic band may be moved depending on whether the elastic band is in contact with the cap hub 120 of the cap 100.

To this end, the engagement ledge 122 for contact with the elastic band 310 is formed on the inner peripheral surface of the cap hub 120.

Accordingly, in a state where the cap 100 is assembled to the injection needle 10, as illustrated in FIG. 2, the elastic band 310 is brought into contact with the engagement ledge 122 and then moved downward in the figure, so that the through-hole 311 is opened.

On the contrary, in a state where the cap 100 is separated from the injection needle 10, as shown in FIG. 3, the elastic band 310 is contracted to its minimum diameter and then rides on the curved surface and is returned to its original position, so that the through-hole 311 is closed.

As a result, a user enables the one-way valve means 300 to intermittently control opening or closing of the through-hole 311 depending on whether the cap 100 is assembled.

Accordingly, when the liquid medicine is intended to be injected into the body and thus the cap 100 is simply separated, the injection flow passage consists of the cylinder 20→the hub 12 of the injection needle 10→the needle body 11 of the injection needle 10, as shown in FIG. 3.

The opening/closing means 400 is fixedly installed within the cap 100 to allow the opening/closing means 400 to be separated together with the cap 100 in response to the separation of the cap 100, thereby enabling the injection needle 10 to be opened.

Accordingly, upon suction of the liquid medicine, the liquid medicine is sucked from the cap 100 into the cylinder through the one-way valve means 300, whereas upon injection of the liquid medicine, the liquid medicine is injected from the cylinder 20 through the opened injection needle 10.

As a result, it is possible to quickly suck and then rapidly discharge the liquid medicine, as required.

Although it has been illustrated that the through-hole 311 is formed in the hub of the injection needle 10 and the configuration in which the cap 100 is coupled outside of the elastic band 310 so as to move the elastic band 310 has been described above, it is also possible to change the position of the through-hole 311.

For example, after the through-hole is formed in the separate connector 500 for connecting the injection needle 10 to the cylinder 20, the cap 100 may be coupled to the connector 500. Alternatively, after the through-hole is formed directly in the cylinder 20 of the syringe, the cap 100 may be coupled to the cylinder 20.

That is, there is no limitation on the positions of the through-hole and the one-way valve means 300 in the present invention.

Next, it is contemplated to employ a one-way valve means 300 which is opened by a negative pressure applied in the syringe and is closed by a positive pressure applied in the syringe. This one-way valve means may be implemented in various ways as being automatically opened or closed merely depending on the direction of pressure applied in the syringe without a additional manipulation.

Particularly, in the present invention, the one-way valve means 300 is preferably a well-known check valve including an elastic flap 320 configured to selectively open or close the through-hole 311 as shown in FIGS. 5 and 6.

Furthermore, a description of a configuration overlapping with that of the embodiment which employs the one-way valve means 300 opened or closed depending on whether the aforementioned cap 100 is coupled will be omitted, and only an operation of the one-way valve means 300 which is different from that in the embodiment will be described below.

A sealing means 600 such as a separate elastic seal may be additionally provided between the inner peripheral surface of the cap hub 120 and the outer peripheral surface of the hub 12 to prevent the liquid medicine from leaking through a gap therebetween Even in this case, the suction flow passage consists of the suction needle 110 of the cap 100→the cap hub 120 of the cap 110→one-way valve means 300→the hub 12 of the injection needle 10→the cylinder 20.

In addition thereto, the one-way valve means 300 that communicates with the through-hole 311 and thus is automatically opened or closed depending on the direction of pressure on the liquid medicine is embedded in the hub 12 of the injection needle 10.

As shown in FIGS. 5 and 6, this one-way valve means 300 may include a circular elastic flap 320, which is made of, for example, a flexible material such as silicone, and a stepped portion 321.

The elastic flap 320 is formed to have a diameter corresponding to an inner diameter of the hub 12 so that a center portion of the elastic flap is assembled and fixed in the hub 12, and the stepped portion 321 is formed above an outer peripheral edge of the elastic flap 320 so as to limit upward deformation of the elastic flap 320.

As a result, upon suction of the liquid medicine, the one-way valve means 300 is opened while the outer peripheral edge of the elastic flap 320 is deformed downward as shown in FIG. 5, so that the cylinder 20 of the syringe is filled with the liquid medicine through the suction flow passage.

Moreover, as shown in FIG. 6, the injection flow passage consists of the cylinder 20→the hub 12 of the injection needle 10→the needle body 11 of the injection needle 10.

Since the outer peripheral edge of the elastic flap 320 in the one-way valve means 300 is contacted with the stepped portion 321 to limit upward deformation of the elastic flap 320 as shown in FIG. 6, the one-way valve means 300 is closed to prevent the liquid medicine from leaking to the suction flow passage.

Accordingly, upon suction of the liquid medicine, the liquid medicine is sucked from the cap 100 into the cylinder through the one-way valve means 300, and upon injection of the liquid medicine, the liquid medicine is injected from the cylinder 20 through the injection needle 10.

As a result, it is possible to easily perform the injection of the liquid medicine while further smoothly performing the suction of the liquid medicine.

Although the configuration in which the through-hole 311 and the one-way valve means 300 are placed in the hub 12 has been described above by way of example, the through-hole 311 and the one-way valve means 300 may be placed in the cylinder 20 or in the separate connector 500 for coupling the injection needle 10 to the cylinder 20. In this case, the through-hole 311 is connected directly to the inside of the cap 100.

Moreover, FIG. 7 shows that one-way valve means 300 in the form of an elastic band 310 and an elastic flap 320 are formed in a dual configuration. In this case, a first one-way valve means 300 formed with modified through-holes 311 and groove 312 may be provided on the hub 12 of the injection needle 10, and opening or closing of the first one-way valve means 300 can be controlled depending on whether the cap 100 is assembled. A second one-way valve means 300 comprised of the elastic flap 320 having a modified shape may be provided within the hub 12.

As for the second one-way valve means 300, the elastic flap 320 does not require the separate stepped portion, and a generally inclined wing-shaped portion of the elastic flap is brought into direct contact with an inner wall of the hub 12 depending on the direction of pressure on the liquid medicine, thereby performing the opening or closing of the second one-way valve means 300.

As such, it is also possible to configure the syringe by including two or more one-way valve means 300.

Next, an example in the first embodiment of the syringe according to the present invention, which employs a one-way valve means 300 opened or closed by changing alignment of flow passages in response to a user's rotation manipulation, will be described with reference to FIGS. 8 and 9.

Even in this case, the suction flow passage consists of the suction needle 110 of the cap 100→the cap hub 120 of the cap 100→the one-way valve means 300→the hub 12 of the injection needle 10→the cylinder 20.

The through-hole 311 which communicates with the inside of the cap hub 120 is formed in a generally "L" shape in the hub 12 of the injection needle 10, and an opening 330 is formed in the cylinder 20 of the syringe to correspond to the through-hole 311.

Accordingly, when the cylinder 20 is rotated and then the opening 330 and the through-hole 311 are aligned as shown in FIG. 8, the liquid medicine can be sucked. When the cylinder 20 is further rotated to release the alignment, the opening 330 and the through-hole 311 are not aligned with each other and thus are blocked as shown in FIG. 9, so that a backflow of the liquid medicine to the suction flow passage is prevented upon injection of the liquid medicine.

Although the one-way valve means 300 has been described as being also placed in the hub 12 by way of example, the one-way valve means 300 may be placed in the cylinder 20 or the separate connector 500 for connecting the injection needle 10 to the cylinder 20.

Next, an example in the first embodiment of the syringe according to the present invention in which the one-way valve means 300 is externally provided is illustrated in FIGS. 10 to 12.

Although the examples in which the one-way valve means 300 is embedded in the cap 100 or the injection needle 10 have been described above, a force required for sucking the liquid medicine may be utilized when the liquid medicine passes through the one-way valve means 300.

That is, although the one-way valve means 300 is necessarily designed to be large in size so as to perform suction of the liquid medicine with a smaller force, the one-way valve means 300 is embedded in an conventional syringe, whereby there is limitation on enlargement of the syringe in size.

Therefore, in the present invention, as shown in FIGS. 10 to 12, the through-hole 311 may be formed in the cap hub 120 of the cap 100 to add an external suction flow passage extending from the through-hole 311 to the cylinder 20 of the syringe.

In this way, it is possible to eliminate limitation on the size of the one-way valve means 300.

FIG. 10 illustrates an example in which the one-way valve means 300 is separately provided outside.

The one-way valve means 300 may be variously modified to, for example, a check valve having a sphere illustrated in FIG. 11 embedded therein and no limitation on the size thereof, other than the aforementioned examples.

For example, as shown in FIG. 10, the one-way valve means 300 is a known check valve including the sphere 340 for selectively opening and closing a flow passage connected to the through-hole 311.

The check valve including the sphere 340 has valve seats 341 and 342 on both sides of the movable sphere 340, wherein one of the valve seat 341 is formed to have a cut-out portion so as to allow a flow of the liquid medicine and the opposite valve seat 332 is configured to contact an outer surface of the sphere 340, thereby maintaining airtightness.

As a result, when a negative pressure is applied in the cylinder 20 of the syringe, the sphere 340 is moved toward the cut-out valve seat 341 so that the liquid medicine can flow through the cut-out portion; whereas when a positive pressure is applied in the cylinder 20 of the syringe, the sphere 340 is moved toward the valve seat 342 to maintain airtightness, thereby blocking the flow of the liquid medicine.

In this case, an additional structure for forming a flow passage between the cap 100 and the cylinder 20 may be added.

For example, a branch tube may be formed integrally with each of the cap hub 120 and the cylinder 20 and the branch tubes of them may be then connected by a flexible tube made of a flexible material to each other. In addition, the branch tubes may be configured to be at certain angles and may also have a well-known configuration enabling selective connection or disconnection of the branch tubes.

In the configuration for disconnecting the tubes from each other, there would no leakage of the liquid medicine only if a state where the one-way valve means 300 is connected to the cylinder 20 should be maintained.

Moreover, FIG. 10 shows that only the one-way valve means 300 is externally provided, and FIG. 12 shows an example in which the one-way valve means 300 is externally provided by using the separate connector 500.

This connector 500 may be formed integrally with the cap hub 120 or the cylinder 20, the one-way valve means 300 may be embedded in the connector 500, and there will be no limitation on modification thereof.

(2) Second Embodiment

Example in which the inlet of the suction flow passage and the outlet of the injection flow passage are not coaxially arranged with each other, and the outlet of the suction flow passage and the inlet of the injection flow passage are shared.

Next, the second embodiment of the present invention is a case in which the outlet of the suction flow passage and the inlet of the injection flow passage are shared, whereas the inlet of the suction flow passage and the outlet of the injection flow passage are not coaxially arranged with each other.

To this end, the cap 100 and the injection needle 10 are independently placed, and the opening/closing means 400 is separated from the cap 100 and is provided to close the injection needle 10.

In this case, as shown in FIG. 13, the one-way valve means 300 is provided on the suction flow passage. The suction flow passage extending from the cap 100 to the cylinder 20 may be constructed with the flexible tube, although it will be also possible to configure this suction flow passage to be maintained at a certain angle different from that of the flow passage from the cylinder 20 to the injection needle 10.

Accordingly, the suction flow passage may be formed at one of bodies branched at different angle from the cylinder 20, and the injection flow passage may be formed at the other of the bodies.

With this configuration, the liquid medicine is sucked through the cap 100 in a state where the injection flow passage is closed by the opening/closing means 400, whereby the sucked liquid medicine passes through the one-way valve means 300 and fills the cylinder 20, and the liquid medicine to be injected may be discharged to the injection needle 10 from which the opening/closing means 400 has been removed.

FIG. 14 shows a configuration in which the separate connector 500 is added, and illustrates the connector 500 having a perpendicular branch, but the connector may be configured to have a differently angled branch, or it is also preferable to configure the connector to have an angle-adjustable branch. It is also possible to provide the one-way valve means 300 within the connector 500.

(3) Third Embodiment

Example in which the inlet of the suction flow passage and the outlet of the injection flow passage are coaxially arranged with each other, and the outlet of the suction flow passage and the inlet of the injection flow passage are not shared.

FIG. 15 illustrates a case in which the inlet of the suction flow passage and the outlet of the injection flow passage are coaxially arranged with each other as described above, whereas the outlet of the suction flow passage and the inlet of the injection flow passage are not shared.

In this case, the one-way valve means 300 may be embedded or externally provided as illustrated in the figure.

Even in this case, a branch tube may be formed integrally with each of the cap hub 120 and the cylinder 20 and the branch tubes of them may be then connected by a flexible tube made of a flexible material to each other. In addition, the branch tubes may be configured to be at certain angles and may also have a well-known configuration enabling selective connection or disconnection of the branch tubes.

The one-way valve means 300 may be comprised of a soft elastic sealing material 350 and a pointed penetration needle 351 configured to penetrate and be inserted into or to be detachable from the soft sealing material 350.

For example, if the cylinder 20 is provided with the elastic sealing material 350 such as silicone and the pointed penetration needle 351 for penetrating the sealing material is also provided separately, in a state where the penetrating needle 351 penetrates and is placed in the elastic sealing material 350 as in a vial, for example, the liquid medicine can be sucked into the cylinder 20. When the penetration needle 351 is separated from the elastic sealing material 350, an aperture in the elastic sealing material 350 generated by the penetration of the penetration needle is clogged to prevent the liquid medicine in the cylinder 20 from leaking through the elastic sealing material 350.

(4) Fourth Embodiment

Example in which the inlet of the suction flow passage and the outlet of the injection flow passage are not coaxially arranged with each other, and the outlet of the suction flow passage and the inlet of the injection flow passage are not shared.

Finally, the fourth embodiment is a case in which, as shown in FIG. 16, the inlet of the suction flow passage and the outlet of the injection flow passage are not coaxially arranged with each other, and the outlet of the suction flow passage and the inlet of the injection flow passage are not shared.

Although FIG. 16 shows the example in which the one-way valve means 300 is embedded in the cap 100, the one-way valve means 300 may be formed in the flow passage extending from the cap 100 to the cylinder 20 or may be provided in the cylinder 20.

Again, as described above, the one-way valve means 300 may be implemented with the elastic sealing material 350 and the pointed penetration needle 351.

As a result, the liquid medicine sucked into the cap 100 is then sucked into the cylinder 20 through the one-way valve means 300, and the liquid medicine in the cylinder 20 can be injected into the body via the injection needle 10 by removing the opening/closing means 400.

In this case, the suction flow passage and the injection flow passage are formed completely independently.

Therefore, the syringe of the present invention has great advantages in that by additionally forming the suction flow passage including the cap 100 so as not to pass through the injection needle 10 and by adding the opening/closing means 400 configured to temporarily close the injection needle 10, the suction of the liquid medicine is not limited to passage of the injection needle 10 as in an conventional syringe, so that the suction of the liquid medicine can be smoothly performed with a smaller force.

In addition, there is a great advantage in that by externally providing the one-way valve means 300, if necessary, it is possible to more quickly and smoothly suck the liquid medicine without being limited by the size of the one-way valve means 300.

The aforementioned embodiments are merely examples for specifically explaining the spirit of the present invention, and the scope of the present invention is not limited to the figures and embodiments.

[Explanation of Reference Numerals]

| | |
|---|---|
| 10: Injection needle | 11: Needle body |
| 12: Hub | 13: Adhesive material |
| 20: Cylinder | 30: Plunger |
| 100: Cap | 110: Suction needle |
| 120: Cap hub | 122: Engagement ledge |
| 300: One-way valve means | 310: Elastic band |
| 311: Through-hole | 312: Groove |
| 320: Elastic flap | 321: Stepped portion |
| 330: Opening | 340: Sphere |
| 341, 342: Valve seat | 350: Elastic sealing member |
| 351: Penetration needle | 400: Opening/closing means |
| 410: Hermetic space | 420: Flange |
| 500: Connector | 600: Sealing means |

The invention claimed is:

1. A syringe comprising an injection needle and a cylinder and formed with an injection flow passage extending from the cylinder to the injection needle, the syringe further comprising:
   a detachable opening/closing means for accommodating the injection needle and selectively opening or closing the injection flow passage; and
   a suction flow passage formed from a pointed hollow cap to the cylinder and provided with a through-hole formed in any one of the injection needle, a connector for connecting the injection needle to the cylinder, and the cylinder to establish communication between an inside and an outside thereof and a one-way valve means for intermittently controlling opening or closing of the through-hole,
   wherein a hermetic space is formed at a lower portion of the opening/closing means surrounding a hub of the injection needle to maintain airtightness, and an adhesive material for securing a needle body and the hub of the injection needle to each other is accommodated in the hermetic space of the opening/closing means such that the adhesive material is isolated from the liquid medicine, and
   wherein the opening/closing means is fixedly installed within the cap such that a portion of the suction flow passage is formed in a space between an outer perimeter of the opening/closing means and an inner perimeter of the cap, and the opening/closing means is separated together with the cap in response to separation of the cap.

2. The syringe of claim 1, wherein the one-way valve means is opened in response to coupling of the cap and is closed in response to separation of the cap.

3. The syringe of claim 2, wherein the one-way valve means comprises an elastic band having a circular cross-section and configured to surround and elastically seal the through-hole, an engagement ledge formed on an inner peripheral surface of the cap so as to be brought into contact with and move the elastic band in response to an axial movement of the cap, and a groove configured to elastically return the elastic band to a position at which the elastic band hermetically seals the through-hole.

4. The syringe of claim 1, wherein the one-way valve means is opened by a negative pressure applied in the cylinder of the syringe and is closed by a positive pressure applied in the cylinder of the syringe.

5. The syringe of claim 4, wherein the one-way valve means is a known check valve comprising an elastic flap for selectively opening or closing the through-hole.

6. The syringe of claim 4, wherein the one-way valve means is a known check valve comprising a sphere for selectively opening or closing the through-hole.

7. The syringe of claim 1, wherein the one-way valve means is opened or closed depending on a change in alignment of the flow passages in response to a rotation manipulation.

8. The syringe of claim 1, wherein the one-way valve means comprises an elastic sealing member fixed to maintain airtightness of the through-hole and a penetration needle configured to penetrate the elastic sealing member, whereby the one-way valve means is opened in response to insertion of the penetration needle into the elastic sealing member and is closed in response to separation of the penetration needle from the elastic sealing member.

* * * * *